(12) United States Patent
Meilan et al.

(10) Patent No.: US 9,334,505 B2
(45) Date of Patent: May 10, 2016

(54) USING CORNGRASS1 TO ENGINEER POPLAR AS A BIOENERGY CROP

(75) Inventors: Richard Meilan, West Point, IN (US); Peter Marius Rubinelli, Fayetteville, AR (US); George Chuck, Berkeley, CA (US)

(73) Assignees: PURDUE RESEARCH FOUNDATION, West Lafayette, IN (US); THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 409 days.

(21) Appl. No.: 13/571,900

(22) Filed: Aug. 10, 2012

(65) Prior Publication Data

US 2013/0042372 A1 Feb. 14, 2013

Related U.S. Application Data

(60) Provisional application No. 61/522,921, filed on Aug. 12, 2011.

(51) Int. Cl.
*C12N 15/82* (2006.01)
*A01H 5/00* (2006.01)

(52) U.S. Cl.
CPC .......... *C12N 15/8255* (2013.01); *C12N 15/827* (2013.01); *C12N 15/8218* (2013.01); *C12N 15/8245* (2013.01); *C12N 15/8261* (2013.01)

(58) Field of Classification Search
None
See application file for complete search history.

(56) References Cited

U.S. PATENT DOCUMENTS

| 6,855,864 | B2 | 2/2005 | Chiang et al. |
| 7,057,087 | B2 | 6/2006 | Podila et al. |
| 7,148,406 | B2 | 12/2006 | Helentjaris et al. |
| 2006/0236427 | A1* | 10/2006 | Chiang et al. ............... 800/284 |
| 2008/0213871 | A1* | 9/2008 | Sticklen ..................... 435/277 |
| 2008/0256664 | A1* | 10/2008 | Weigel et al. ............... 800/278 |

OTHER PUBLICATIONS

Chuck et al, 2007, Nat. Gen., 39:544-549.*
Hake et al, 2010, An Assessment of the biofuel properties of crop plants fixed in the juvenile phase of development through over-expression of the Corngrass1 gene, 2010 Physical Biosciences Research Meeting.*
Xie et al, 2006, Plant Phys., 142:280-293.*
Busov, Victor, et al., Activation tagging is an effective gene tagging system in Populus, Tree Genetics & Genomes (2011) 7:91-101.
Chuck, George, The heterochronic maize mutant Corngrass1 results from overexpression of a tandem microRNA, Nature Genetics (Apr. 2007) 39(4):544-549.
Guo, An-Yuan, et al., Genome-wide identification and evolutionary analysis of the plant specific SBP-box transcription factor family, Gene (2008) 418:1-8.
Harfouche, Antoine, et al., Tree genetic engineering and applications to sustainable forestry and biomass production, Trends in Biotechnology (Jan. 2011) 29:9-17.
Meilan, R. et al. Poplar (*Populus* spp). Methods in Molecular Biology, Agrobacterium Protocols, vol. 344, pp. 143-151, 2007.

* cited by examiner

*Primary Examiner* — David H Kruse
*Assistant Examiner* — Jason Deveau Rosen
(74) *Attorney, Agent, or Firm* — Marianne Fuierer; Moore & Van Allen, PLLC

(57) ABSTRACT

Embodiments of the present invention relate generally to new bioenergy crops and methods of creating new bioenergy crops. For example, genes encoding microRNAs (miRNAs) are used to create transgenic crops. In some embodiments, over-expression of miRNA is used to produce transgenic perennials, such as trees, with altered lignin content or composition. In some embodiments, the transgenic perennials are *Populus* spp. In some embodiments, the miRNA is a member of the miR156 family. In some embodiments, the gene is *Zea mays* Cg1.

13 Claims, 7 Drawing Sheets

SMALL RNA NORTHERN BLOT

35S:Cg1 POPLAR PHENOTYPE

- Enlarged, darkened stipules
- Increase in the number of branches (sylleptic shoots) and leaves
- Number of nodes unchanged in many of the transgenic lines Scale bar = 10 cm; ruler = 1 m

FIGURE 3
SUMMARY OF PHENOTYPIC MEASUREMENTS

Severity of phenotype related to *Cg1* expression level (position effects of T-DNA)

| Line | Height (cm) | Stem diam. (mm) | Number of branches | Number of leaves | Number of nodes |
|---|---|---|---|---|---|
| WT 717 | 71.8 ± 5.6 | 4.7 ± 0.6 | 0 | 28.0 ± 3.5 | 34.3 ± 4.9 |
| Cg-10 | 62.9 ± 4.7 | 4.5 ± 0.7 | 0 | 31.0 ± 1.4 | 35.5 ± 0.7 |
| P[a] | 0.16 | 0.81 | - | 0.28 | 0.72 |
| Cg-29 | 60.0 ± 5.5 | 5.0 ± 1.0 | 13.0 ± 2.6 | 88.0 ± 28.2 | 49.3 ± 6.0 |
| P | 0.060 | 0.65 | 0.014 | 0.064 | 0.031 |
| Cg-28 | 52.8 ± 5.7 | 5.0 ± 1.0 | 10.0 ± 1.7 | 79.3 ± 20.5 | 40.0 ± 0.0 |
| P | 0.015 | 0.65 | 0.010 | 0.046 | 0.18 |

[a]P value of Student's t-test

FIGURE 4
PHENOTYPE
Internode Length

| Line | Internode length[a] (5-6) | Internode length (6-7) | Internode length (7-8) | Internode length (8-9) | Plastochron duration (plastochrons/day) |
|---|---|---|---|---|---|
| WT 717 | 6.7 ± 1.2 | 18.0 ± 3.6 | 25.7 ± 3.1 | 25.3 ± 5.0 | 0.24 ± 0.023 |
| Cg-10 | 6.0 ± 1.0 | 11.7 ± 2.3 | 16.7 ± 4.2 | 20.0 ± 3.0 | 0.33 ± 0.077 |
| P | 0.49 | 0.073 | 0.044 | 0.21 | 0.19 |
| Cg-28 | 5.3 ± 1.2 | 9.7 ± 0.58 | 12.7 ± 1.2 | 12.7 ± 1.5 | 0.29 ± 0.098 |
| P | 0.23 | 0.054 | 0.010 | 0.039 | 0.48 |
| Cg-29 | 6.0 ± 1.0 | 8.0 ± 0.0 | 10.3 ± 1.5 | 12.7 ± 1.5 | 0.28 ± 0.053 |
| P | 0.49 | 0.041 | 0.0047 | 0.039 | 0.33 |

[a] All measurements in millimeters.

FIGURE 5
PHENOTYPE
Branching and *Cg1* Expression

Experiment #1

| Line | Branching Phenotype | $C_T$, *Cg1* | $C_T$, *TUA2* | $\Delta C_T$ | $\Delta\Delta C_T$ | Rel. Qty. ($2^{-\Delta\Delta C_T}$) |
|---|---|---|---|---|---|---|
| WT 717 | - | 35.3±1.26 | 22.5±0.49 | 12.8 | 2.00 | 0.250 |
| Cg-10 (calibrator) | - | 34.4±0.31 | 23.6±0.20 | 10.8 | 0 | 1 |
| Cg-11 | - | 31.1±0.56 | 23.5±0.063 | 7.60 | -3.20 | 9.19 |
| Cg-21 | + | 26.7±0.48 | 22.6±0.21 | 4.10 | -6.70 | 104 |
| Cg-28 | + | 26.9±0.23 | 23.6±0.20 | 3.30 | -7.50 | 181 |
| Cg-42 | - | 33.5±0.16 | 23.2±0.0095 | 10.3 | -0.50 | 1.39 |
| Cg-43 | + | 27.2±0.16 | 23.3±0.10 | 3.90 | -6.90 | 119 |
| -neg. control | N.A. | No value returned | 35.6±1.58 | | | - |

Experiment #2

| Line | Branching Phenotype | $C_T$, *Cg1* | $C_T$, *TUA2* | $\Delta C_T$ | $\Delta\Delta C_T$ | Rel. Qty. ($2^{-\Delta\Delta C_T}$) |
|---|---|---|---|---|---|---|
| WT 717 | - | 37.8±2.15 | 29.3±0.27 | 8.50 | 5.40 | 0.0237 |
| Cg-8 | - | 36.9±1.20 | 29.4±0.23 | 7.50 | 4.40 | 0.0474 |
| Cg-10 (calibrator) | - | 32.4±0.89 | 29.3±0.094 | 3.10 | 0 | 1 |
| Cg-29 | + | 29.5±0.51 | 30.7±0.61 | -1.2 | -4.30 | 19.7 |
| Cg-31 | + | 27.5±0.12 | 29.5±0.12 | -2.0 | -5.09 | 34.2 |
| Cg-165 | + | 27.4±0.062 | 29.6±0.30 | -2.20 | -5.30 | 39.4 |
| Cg-180 | - | 36.1±2.39 | 29.3±0.42 | 6.80 | 3.70 | 0.0769 |
| Cg-181 | + | 28.4±2.15 | 29.6±0.26 | -1.20 | -4.30 | 19.7 |
| -neg. control | N.A. | No value returned | 36.2±2.11 | | | - |

LIGNIN ANALYSES

EXPRESSION PATTERNS OF *SBP* GENES

US 9,334,505 B2

USING CORNGRASS1 TO ENGINEER POPLAR AS A BIOENERGY CROP

CLAIM OF PRIORITY UNDER 35 U.S.C. §119

The present application for patent claims priority to and the benefit of the filing date of U.S. Provisional Application No. 61/522,921, entitled "USING CORNGRASS1 TO ENGINEER POPLAR AS A BIOENERGY CROP" filed Aug. 12, 2011, and assigned to the assignee hereof and hereby expressly incorporated by reference herein.

STATEMENT AS TO U.S. GOVERNMENT INTERESTS IN INVENTIONS MADE UNDER FEDERALLY SPONSORED RESEARCH AND DEVELOPMENT

This invention was made with government support under contract number DE-FG02-06ER64301 awarded by the U.S. Department of Energy. The government has certain rights in the invention described herein.

BACKGROUND

Developing alternatives to fossil fuels has long been a worthwhile and valuable goal, especially as obtaining sufficient fossil fuels to meet rising demands promises to become a substantial challenge. Thus, there is a growing demand for biofuels. The U.S. Department of Energy has a set a goal of meeting 20% of U.S. gasoline demand with biofuels, primarily ethanol, by the year 2020.

In 2006, it was predicted that large quantities of ethanol would be produced in the future because of two federal actions. The two actions are (1) requiring that 7.5 billion gallons of "renewable fuel" be used in gasoline by 2012 (Energy Policy Act (EPACT 2005)) and (2) providing a $0.51 tax credit per gallon of ethanol used as a transportation fuel. As expected, there has been a rapid increase in construction of bio-refineries in the U.S., resulting in achievement of the 8-billion-gallon goal by 2007. These fuel production techniques rely on corn as a feedstock, but these practices are not sustainable.

There are a number of problems with relying on corn as a major source of bioenergy. Corn grain used as a feedstock accounts for the vast majority of ethanol, but there are competing uses (food and feed vs. fuel). The production of enough corn to produce the necessary biofuel is simply not sustainable economically, environmentally, or energetically. Proponents suggest the use of corn stover, which is the residual plant material after ears are removed, can overcome some of these sustainability issues. Unfortunately, this has not been the case.

Government incentives are shifting away from biofuel techniques that rely on corn grain as a feedstock. For example, in the latest Farm Bill, the corn-ethanol subsidy went from $0.51 to $0.45/gallon, and cellulosic ethanol subsidy of $1.01/gallon was instituted. It is clear that a variety of cellulosic feedstocks will be needed.

Thus, there is a need for new bioenergy crops that are sustainable.

BRIEF SUMMARY OF SELECTED EMBODIMENTS OF THE PRESENT INVENTION

Embodiments of the present invention relate generally to new bioenergy crops and methods of creating new bioenergy crops. For example, genes encoding microRNAs (miRNA) are used to create transgenic crops. In some embodiments, over-expression of miRNA is used to engineer perennials, such as trees, with altered lignin content or composition. In some embodiments, the perennials are *Populus* spp.

In one embodiment, a method of producing a poplar plant with altered lignin content or composition as compared to a control poplar plant, comprising inserting a gene encoding a miRNA into a construct, introducing the construct into a cell to yield a transformed cell, generating a transgenic poplar plant from the transformed cell, and growing the transgenic poplar plant, wherein the transgenic poplar plant exhibits altered lignin content or composition as compared to the control poplar plant. In some embodiments, the miRNA is a member of the 156 miRNA family (miR156).

In some embodiments, the transgenic poplar plant exhibits decreased lignin content as compared to the control poplar plant. In some embodiments, the transgenic poplar plant exhibits increased lignin content as compared to the control poplar plant. In some embodiments, the transgenic poplar plant exhibits a lignin composition having an increased ratio of syringyl units to guaiacyl units (S/G ratio) as compared to the control poplar plant. In some embodiments, the transgenic poplar plant exhibits a lignin composition having a decreased S/G ratio as compared to the control poplar plant. In some embodiments, the transgenic poplar plant exhibits altered reproductive capacity as compared to the control poplar plant.

In one embodiment, the insertion of the gene results in transgenic plants having at least one of multiple stems, faster growth, higher carbohydrate levels, and no or delayed flowering.

In one embodiment, the miRNA targets a gene having an SBP box, thereby affecting expression of the gene having the SBP box. In some embodiments, the gene having the SBP box is expressed in a tissue-specific gene. Examples of tissues in which genes having an SBP box are expressed include shoot apex, leaf, petiole, node, and internode. Examples of genes containing an SBP box include SBP4 and SBP5. At least 14 poplar genes contain an SBP box, which is a highly conserved DNA-binding domain.

In another embodiment, the present invention comprises a method of producing a poplar plant with altered lignin content or composition as compared to a control poplar plant, comprising inserting a gene encoding Corngrass1 (Cg1) into a construct; introducing the Cg1 construct into a cell to yield a transformed cell; generating a transgenic poplar plant from the transformed cell; and growing the transgenic poplar plant, wherein the transgenic poplar plant exhibits altered lignin content or composition as compared to the control poplar plant. In some embodiments, the Cg1 gene originates from *Zea mays*. In some embodiments, the Cg1 gene is a gene homologous to the *Zea mays* Cg1 gene. The homology may be as high as, for example, 60, 65, 70, 75, 80, 85, 80, 95, or 100% at the amino acid sequence level. In some embodiments, the Cg1 gene is SEQ ID NO: 1.

In some embodiments, the transgenic poplar plant exhibits decreased lignin content as compared to the control poplar plant. In some embodiments, the transgenic poplar plant exhibits increased lignin content as compared to the control poplar plant. In some embodiments, the transgenic poplar plant exhibits a lignin composition having an increased ratio of syringyl units to guaiacyl units as compared to the control poplar plant. In some embodiments, the transgenic poplar plant exhibits a lignin composition having a decreased ratio of syringyl units to guaiacyl units as compared to the control poplar plant. In some embodiments, the transgenic poplar plant exhibits altered reproductive capacity as compared to the control poplar plant.

In one embodiment, the insertion of the Cg1 gene results in transgenic plants having at least one of multiple stems, faster growth, higher carbohydrate levels, and no or delayed flowering. In some embodiments, the insertion of the Cg1 gene results in transgenic plants having multiple stems that do not produce flowers.

In one embodiment, the Cg1 gene targets a gene having an SBP box, thereby affecting expression of the gene having the SBP box. In some embodiments, the gene having the SBP box is expressed in a tissue-specific gene. Examples of tissues in which genes having an SBP box are expressed include shoot apex, leaf, petiole, node, and internode. Examples of genes containing an SBP box include SBP4 and SBP5. At least 14 poplar genes contain an SBP box, which is a highly conserved DNA-binding domain.

In another embodiment, the present invention comprises a transgenic poplar plant comprising a *Zea mays* Cg1 gene. In some embodiments, the transgenic poplar plant further comprises having multiple stems that do not produce flowers. In some embodiments, the transgenic poplar plant has reduced lignin content or altered lignin composition as compared to a control poplar plant. In still other embodiments, the transgenic poplar plant further comprises having at least one of multiple stems, faster growth, higher carbohydrate levels, reduced lignin content, altered lignin composition, and no or delayed flowering. In some embodiments, the transgenic poplar plant further comprises altered reproductive capacity.

In another embodiment, the present invention comprises a transgenic poplar plant containing a polynucleotide comprising: (a) SEQ ID NO:1 (b) the full-length complement of SEQ ID NO:1 (c) the reverse full-length complement of SEQ ID NO:1 or (d) the reverse full-length sequence of SEQ ID NO: 1.

In another embodiment, the present invention comprises a transgenic poplar plant comprising any portion of (a) SEQ ID NO:1 (b) the full-length complement of SEQ ID NO:1 (c) the reverse full-length complement of SEQ ID NO:1 or (d) the reverse full-length sequence of SEQ ID NO: 1 and having at least one of multiple stems, faster growth, higher carbohydrate levels, reduced lignin content, altered lignin composition, and no or delayed flowering.

In another embodiment, the present invention comprises a transgenic poplar plant comprising a nucleotide sequence containing a member of the miR156 family. In some embodiments, the transgenic poplar plant further comprises having at least one of multiple stems, faster growth, higher carbohydrate levels, reduced lignin content, altered lignin composition, and no or delayed flowering.

BRIEF DESCRIPTION OF THE SEVERAL VIEWS OF THE DRAWINGS

Figure 1:
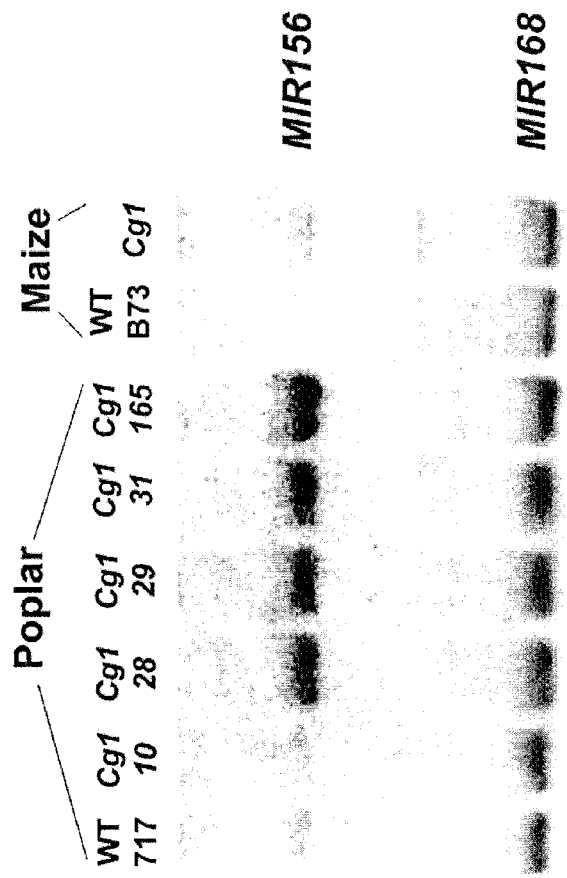
Figure 2:
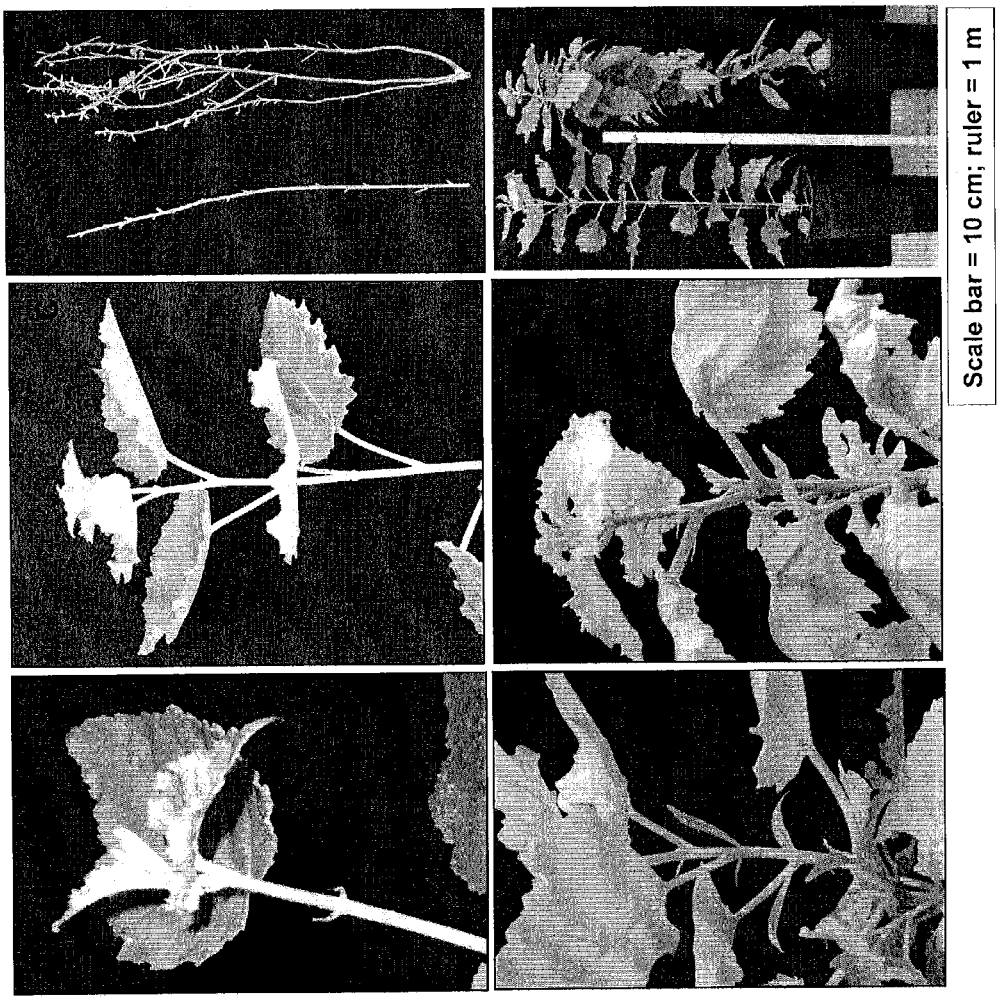
Figure 6:
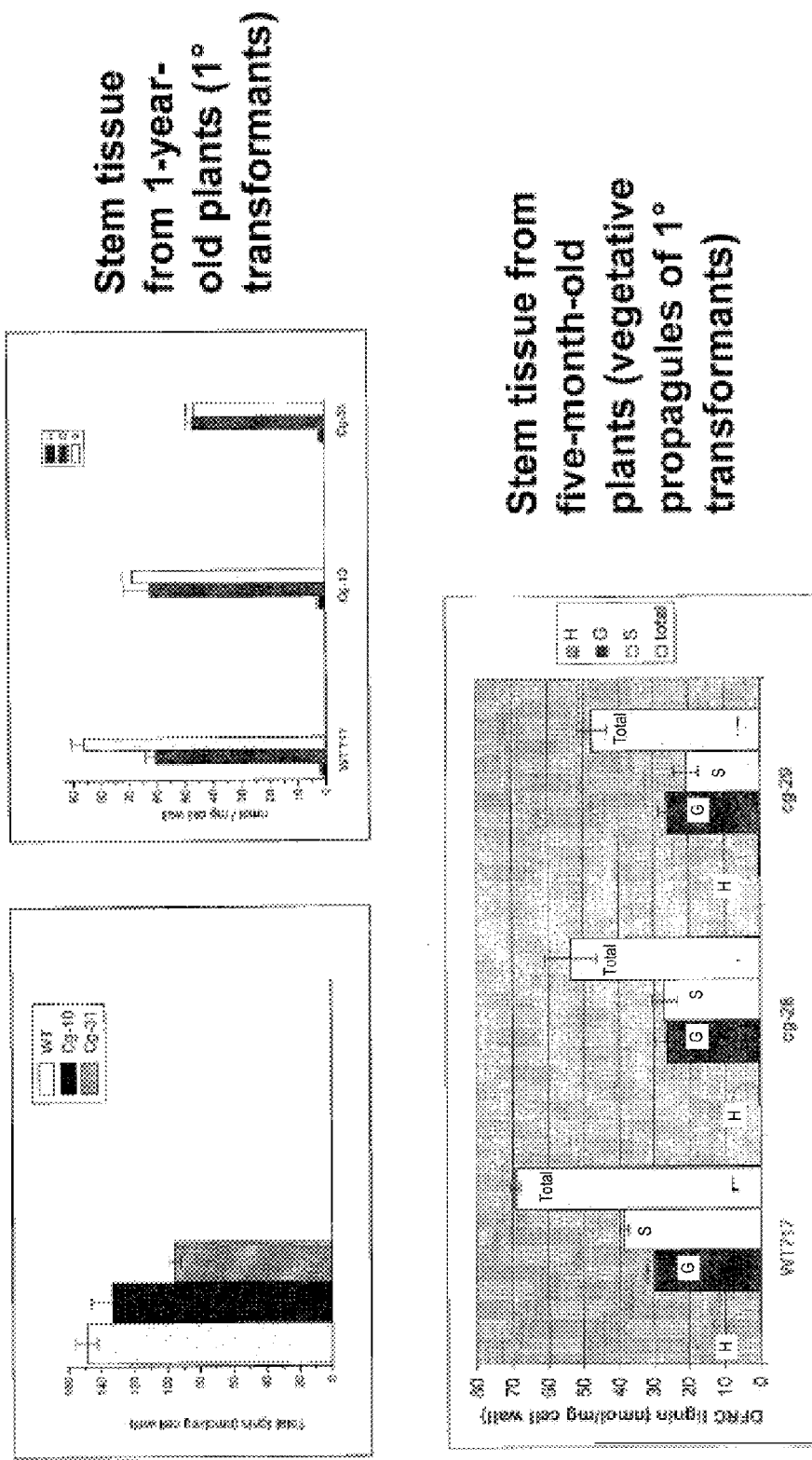
Figure 7:
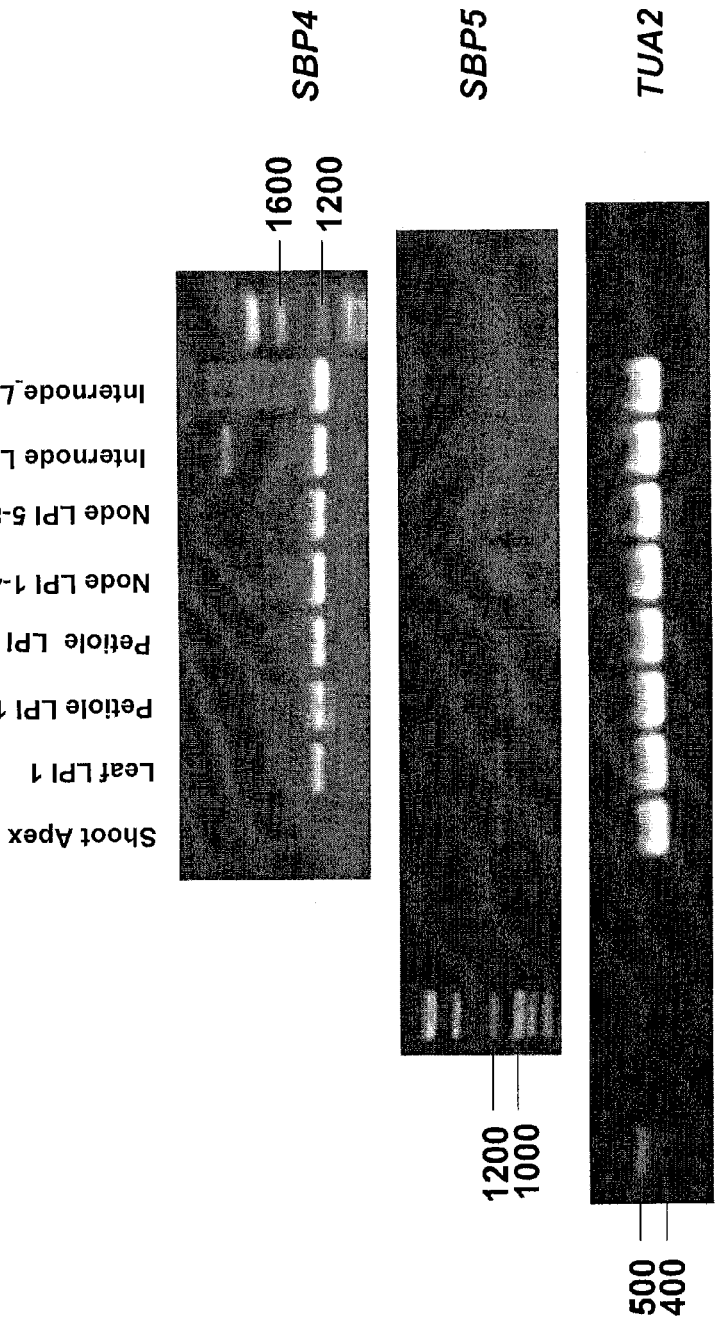

Having thus described embodiments of the present invention in general terms, reference will now be made to the accompanying drawings, which are not necessarily draw to scale, and wherein:

FIG. 1 shows expression of mature miRNA of poplar 35S: Cg1 lines in accordance with embodiments of the present invention;

FIG. 2 shows phenotypes of poplar 35S:Cg1 lines in accordance with embodiments of the present invention;

FIG. 3 illustrates a summary of phenotypic measurements of poplar 35S:Cg1 lines, in accordance with embodiments of the present invention;

FIG. 4 shows internode length measurements of poplar 35S:Cg1 lines, in accordance with embodiments of the present invention;

FIG. 5 shows branching and Cg1 expression of poplar 35S:Cg1 lines, in accordance with embodiments of the present invention;

FIG. 6 shows lignin analyses of poplar 35S:Cg1 lines, wherein H is amount of p-hydroxyphenyl (nmol/mg cell wall), G is amount of guaiacol (nmol/mg cell wall), S is amount of syringyl (nmol/mg cell wall), and T is total amount of lignin (nmol/mg cell wall), in accordance with embodiments of the present invention; and FIG. 7 shows expression of two SBP genes in accordance with embodiments of the present invention.

DETAILED DESCRIPTION OF EMBODIMENTS OF THE PRESENT INVENTION

Embodiments of the present invention now will be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Additionally, while embodiments are disclosed as "comprising" elements, it should be understood that the embodiments may also "consist of" elements or "consist essentially of" elements. Where possible, any terms expressed in the singular form herein are meant to also include the plural form and vice versa unless explicitly stated otherwise. Also, as used herein, the term "a" and/or "an" shall mean "one or more," even though the phrase "one or more" is also used herein. Like numbers refer to like elements throughout.

Embodiments of the present invention relate generally to new bioenergy crops and methods of creating new bioenergy crops. Transgenic microRNA expression in plants is a promising technique for creating new bioenergy crops with desired traits. Examples of desirable traits for bioenergy crops include, but are not limited to, crops that are vegetatively propagated (have rooting ability); have rapid growth; have high conversion efficiency for achieving a state appropriate for the final end use; have reduced lignin content or altered lignin composition; have reproductive sterility to prevent diversion of carbohydrate away from vegetative growth and to prevent unwanted spread of the transgene (i.e., transgene confinement); and have biomass distributed across several stems to provide ease of harvesting.

MicroRNAs (miRNAs) are small, non-coding and regulatory RNAs that are naturally occurring and control developmental timing in animals such as *C. elegans* and *Drosophila*, and in plants such as *Arabidopsis thaliana, Zea mays, Antirrhinum majus*, and *Petunia hybrida*. Naturally occurring miRNAs often have stage- or tissue-specific expression. Post-transcriptional control occurs due to hairpin precursor formed as a result of inverted repeat, as it gets cleaved and unwound. Post-transcriptional control occurs also due to the miRNAs hybridizing to mRNA for degradation of target gene. Control can also be at the level of translation, depending on the degree of complementarity of the binding site to the miRNA.

In some embodiments, the crops of the present invention are woody perennials, such as trees. It is well known that lignin is one of the main components of plant cell walls, along with cellulose and hemicellulose. Lignin, a complex phenolic polymer, is a major part of the supportive structure of most woody plants including angiosperm and gymnosperm trees.

Lignin generally constitutes about 25% of the dry weight of the wood, making it the second most abundant organic compound on earth after cellulose. Lignin provides rigidity to wood for which it is well suited due, in part, to its resistance to biochemical degradation. However, lignin serves as a detriment to the use of woody perennials for end uses such as bioenergy crops, since the presence of lignin necessitates further processing of the plant material before it can be used for its intended purpose. Development of trees with altered lignin content or composition is therefore desirable as it improves conversion efficiency of processing, possibly by reducing or removing the need for pretreatment.

In some embodiments, miRNA over-expression is used to produce perennials with altered lignin content or composition. Woody perennials such as poplars (*Populus* spp.) are appealing candidates for creating new bioenergy crops. As used herein, the term "poplar" or "poplar plant" refers to all of the *Populus* spp., including hybrids.

In one embodiment, a method of producing a poplar plant with altered lignin content or composition as compared to a control poplar plant, comprising inserting a gene encoding a miRNA into a construct, introducing the construct into a cell to yield a transformed cell, generating a transgenic poplar plant from the transformed cell, and growing the transgenic poplar plant, wherein the transgenic poplar plant exhibits altered lignin content or composition as compared to the control poplar plant. As is well known to those of ordinary skill in the art, a construct comprises a plasmid or vector containing a gene of interest along with promoter and regulator sequences essential to expression and regulation of the gene of interest in the recipient cell.

In some embodiments, the miRNA is a member of the miR156 family, which is a highly conserved family of miRNAs. Members of the miR156 family exist as tandem repeats.

In some embodiments, the transgenic poplar plant exhibits altered lignin content or composition in the form of decreased lignin content as compared to the control poplar plant. In some embodiments, the transgenic poplar plant exhibits altered lignin content or composition in the form of increased lignin content as compared to the control poplar plant. In some embodiments, the transgenic poplar plant exhibits altered lignin content or composition in the form of a lignin composition having an increased ratio of syringyl units to guaiacyl units as compared to the control poplar plant. In some embodiments, the transgenic poplar plant exhibits altered lignin content or composition in the form of a lignin composition having a decreased ratio of syringyl units to guaiacyl units as compared to the control poplar plant. The control poplar plant can be a wild-type plant, a calibrator transgenic line, or any other poplar plant suitable for the purpose of comparison.

In one embodiment, the insertion of the gene results in transgenic plants having at least one of multiple stems, faster growth, higher carbohydrate levels, and no or delayed flowering. In one embodiment, the insertion of the gene results in transgenic plants having altered reproductive capacity.

In one embodiment, the gene encoding the miRNA is under the control of a constitutive promoter. In some embodiments, the constitutive promoter is the cauliflower mosaic virus 35S promoter.

In one embodiment, the gene encoding the miRNA is under the control of a tissue-specific promoter. In one embodiment, the gene encoding the miRNA is under the control of a temporal-specific promoter.

In one embodiment, the miRNA targets a gene having an SBP box, thereby affecting expression of the gene having the SBP box. The SPB box is a DNA-binding domain. The term "targets" refers to the fact that the expressed miRNA binds to the SBP box or in some other way interferes with the normal expression or function of the genes containing the SBP box. In some embodiments, the gene containing the SBP box is expressed in a tissue-specific gene. Examples of tissues in which genes having an SBP box are expressed include shoot apex, leaf, petiole, node, and internode. Examples of genes containing an SBP box include SBP4 and SBP5. At least 14 poplar genes contain an SBP box.

Poplar is an attractive option for a bioenergy crop for a number of reasons, including the following: it is a perennial that redistributes minerals and nutrients on an annual basis, reducing the need for supplemental fertilizer treatments.

Harvesting and handling options available for poplar increase landowner choices and profitability. For example, poplar is harvested on multi-year rotations, reducing the amount of annual disturbance. Also, if feedstock prices are low, *Populus* stems can be "stored on the stump" as it is easy to store and maintains stability during storage. Finally, there is flexibility with regard to timing of harvest (e.g., can occur in winter), so that harvest can be timed to suit other needs.

Poplar provides ease of transformation, in vitro regeneration and ex vitro propagation. There are abundant genomic resources (sequence, microarrays, etc.) available for analyzing poplar. Genotypes are adapted to growing across a wide geographical range and many pedigrees are available, allowing for cultivation of poplar in a wide variety of environments.

As noted above, development of trees with altered lignin content or composition is desirable as it improves conversion efficiency, possibly by reducing or removing the need for pretreatment. In most woody species, such as poplar, lignin is mainly composed of guaiacyl (G) and syringyl (S) units. The availability of woody biomass with high-S lignin increases the yield of biofuel per unit land area because of an increase in conversion efficiency. Woody species with high-S lignin show an increased S/G ratio. However, trees with a lower S/G ratio can also show an increase in conversion efficiency, particularly if the overall level of lignin is decreased.

A number of binary vectors for lignin modification are known. As is understood by one of ordinary skill in the art, each of the known binary vectors can be used in combination with miRNAs to modulate lignin content and composition in transgenic plants Corngrass1 (Cg1) is a gene isolated from corn (*Zea mays* L.) that encodes a miRNA that controls the expression of several genes, including some that specify meristem fate. Specifically, Cg1 is a member of the miR156 family and encodes two tandem miR156 genes that are over-expressed in the meristem and lateral organs. In some plant systems, constitutive expression (high levels of expression in all tissues at all times) of the Cg1 gene has led to multiple stems (i.e., a loss of apical dominance), faster vegetative growth, reproductive sterility, and lower levels of lignin. The Cg1 gene was discovered by Dr. George Chuck of the Plant Gene Expression Center in Albany, Calif. Dr. Chuck provided the binary vector construct described below and used in the examples herein. Dr. Chuck's work with the Cg1 gene and the patent application(s) currently in preparation for Dr. Chuck's Cg1 work are all incorporated herein by reference in their entirety.

In another embodiment, the present invention comprises a method of producing a poplar plant with altered lignin content or composition as compared to a control poplar plant, comprising inserting a gene encoding Cg1 into a construct, introducing the Cg1 construct into a cell to yield a transformed cell, generating a transgenic poplar plant from the transformed cell and growing the transgenic poplar plant, wherein the transgenic poplar plant exhibits altered lignin content or composition as compared to the control poplar plant. In some embodiments, the Cg1 gene originates from corn. In some embodiments, the Cg1 gene is a gene highly homologous to the corn Cg1 gene. The homology may be as high as, for example, 60, 65, 70, 75, 80, 85, 80, 95, or 100% at the amino acid sequence level. In some embodiments, the Cg1 gene is SEQ ID NO:1.

In some embodiments, the Cg1 transgenic poplar plant exhibits altered lignin content or composition in the form of decreased lignin content as compared to the control poplar plant. In some embodiments, the Cg1 transgenic poplar plant exhibits altered lignin content or composition in the form of an increased lignin content as compared to the control poplar plant. In some embodiments, the Cg1 transgenic poplar plant exhibits altered lignin content or composition in the form of a lignin composition having an increased ratio of syringyl units to guaiacyl units as compared to the control poplar plant. In some embodiments, the Cg1 transgenic poplar plant exhibits altered lignin content or composition in the form of a lignin composition having a decreased ratio of syringyl units to guaiacyl units as compared to the control poplar plant. The control poplar plant can be a wild-type plant, a calibrator transgenic line (a transgenic line that does not express the transgenic gene), or any other poplar plant suitable for the purpose of comparison.

In one embodiment, the insertion of the Cg1 gene results in transgenic plants having at least one of multiple stems, faster growth, higher carbohydrate levels, and no or delayed flowering. In one embodiment, the insertion of the Cg1 gene results in transgenic plants having altered reproductive capacity.

In one embodiment, the Cg1 gene targets a gene having an SBP box, thereby affecting expression of the gene having the SBP box. In some embodiments, the SBP box targeted is expressed in a tissue-specific gene. Examples of tissues in which genes having an SBP box are expressed include shoot apex, leaf, petiole, node, and internode. Examples of genes containing an SBP box include SBP4 and SBP5. At least 14 poplar genes contain an SBP box.

In another embodiment, the present invention comprises a transgenic poplar plant comprising a *Zea mays* Cg1 gene. In some embodiments, the transgenic poplar plant further comprises having multiple stems that do not produce flowers. In some embodiments, the Cg1 transgenic poplar plant further comprises having reduced lignin content or altered lignin composition as compared to a control poplar plant. In still other embodiments, the transgenic poplar plant further comprises having at least one of multiple stems, faster growth, higher carbohydrate levels, reduced lignin content, altered lignin composition, and no or delayed flowering. In some embodiments, the transgenic poplar plant further comprises altered reproductive capacity.

In another embodiment, the present invention comprises a transgenic poplar plant containing a polynucleotide comprising: (a) SEQ ID NO:1 (b) the full-length complement of SEQ ID NO:1 (c) the reverse full-length complement of SEQ ID NO:1 or (d) the reverse full-length sequence of SEQ ID NO: 1.

In another embodiment, the present invention comprises a transgenic poplar plant comprising any portion of (a) SEQ ID NO:1, (b) the full-length complement of SEQ ID NO:1, (c) the reverse full-length complement of SEQ ID NO:1, or (d) the reverse full-length sequence of SEQ ID NO: 1 and having at least one of multiple stems, faster growth, higher carbohydrate levels, reduced lignin content, altered lignin composition, and no or delayed flowering.

In another embodiment, the present invention comprises a transgenic poplar plant comprising a nucleotide sequence containing a member of the miR156 family. In some embodiments, the member of the miR156 family is Cg1. In some embodiments, the transgenic poplar plant further comprises having at least one of multiple stems, faster growth, higher carbohydrate levels, reduced lignin content, altered lignin composition, and no or delayed flowering.

In one example, the Cg1 gene was inserted, under the control of the constitutive cauliflower mosaic virus 35S promoter, into hybrid aspen genotype INRA 717-1B4 (*Populus tremula×P. alba*). As shown herein, the insertion of the Cg1 gene into hybrid poplar affects the fate of terminal meristems, resulting in plants with multiple stems that do not produce flowers. Over-expression of Cg1 results in poplars with lower levels of lignin than the corresponding non-transgenic control plants.

Transgenic poplar plants were engineered as follows. A 0.6-Kb DNA fragment containing the Cg1 transcript (GenBank Accession #EF541486 and SEQ ID NO:1) was cloned into the binary plasmid pK2GW7 (Karimi M, Inze D, Depicker A. GATEWAY™ vectors for *Agrobacterium*-mediated plant transformation. Trends Plant Sci 2002; 7:193-5, the contents of which are incorporated herein in their entirety) by recombinase-mediated integration using LR clonase (Invitrogen), positioning the Cg1 transcript downstream from the cauliflower mosaic virus 35S promoter and upstream of a 35S terminator.

The sequences of primers used to clone the Cg1 gene into pK2GW7 vector are Cg1 648F: 5-gccggaaacaagctaagacagatgggct (SEQ iD NO:2) and Cg1 64 R: 5'-ctgcctcgtcaatagctgcagtatttgc (SEQ ID NO:3). Primer "Cg1 648 F" is the reverse primer and primer "Cg1 64 R" is the forward primer, relative to the sequence shown in GenBank accession EF541486. "Cg1 648 F" starts at nucleotide position 693 and ends at position 666 of the GenBank sequence. "Cg1 64 R" starts at nucleotide position 74 and ends at position 101 of the GenBank sequence. Thus, the PCR primers create a DNA fragment comprising nucleotides 74-693 of the Cg1 gene shown at GenBank Accession #EF541486 and SEQ ID NO:1.

The pK2GW7 vector containing the Cg1 DNA fragment was transformed into *Agrobacterium tumefaciens* strain GV3101 by electroporation, and transformed cells were selected on solid Luria-Bertani (LB) media containing 100 mg/ml spectinomycin, 50 mg/ml rifampicin, and 50 mg/ml gentamycin. Colonies of transformed *A. tumefaciens* were screened by colony polymerase chain reaction (PCR) for the presence of the Cg1 sequence. PCR-confirmed colonies were grown in liquid medium for 24 hours and cryo-preserved by addition of 25% glycerol (vol/vol) to cultures, followed by storage at −80° C.

One of the PCR-confirmed colonies, designated pGC5.4.9-6-2, was grown for 24 hours in 50 ml of liquid LB medium supplemented with 100 mg/ml spectinomycin, 50 mg/ml rifampicin, and 50 mg/ml gentamycin. Poplar genotype INRA 717-1B4 leaf and stem explants were co-cultivated with this culture, and whole transgenic plants were produced in vitro via organogenesis as described previously (Meilan R, Ma C. Poplar (*Populus* spp.). In: Wang K., ed. *Agrobacterium* Protocols. Totowa, N.J.: Humana Press, 2006, 143-51; the contents of which are incorporated by reference herein in their entirety). A total of five co-cultivations of INRA 717-1B4 with *Agrobacterium* strain pGC5.4.9-6-2 were performed, each using leaf and stem explants from 25 sterile in vitro plant propagules of approx. 9 cm in height. From these co-cultivations, 1,357 explants were obtained, and from these, 29 independent kanamycin-resistant rooted lines (unique transformational events) were produced. All of the transformed plants originated from the single bacterial cell pGC5.4.9-6-2, as noted above. The lines comprise unique transformational events because each of the 29 lines originated from a single plant co-cultivated with pGC5.4.9-6-2. Transgenic lines were confirmed by PCR amplification of Cg1 from genomic DNA extracted from leaves of the in vitro-grown, kanamycin-resistant rooted plants.

The presence of the transgene was verified via standard PCR. A northern blot showed that the Cg1 message was processed to produce a mature miRNA, as shown in FIG. 1. Expression of MIR168 was used as a loading control. As can be seen in FIG. 1, the wild-type poplar (WT 717) and the Cg1-10 transgenic line do not have the MIR156 message, nor do the maize (corn) samples. The WT 717 and Cg1-10 samples serve as controls. Cg1-10 is a transgenic line that does not express the Cg1 gene. However, poplar transgenic lines Cg1-28, Cg1-29, Cg1-31, and Cg1-165 exhibit the presence of mature Cg1 miRNA.

As described above, the transformed Cg1 construct was introduced into the poplar hybrid aspen genotype INRA 717-1B4 under control of the constitutive 35S promoter to create a gene construct in which the Cg1 gene inserted is constitutively expressed in the transgenic poplar. These lines are referred to as the 35S:Cg1 lines. As seen in FIG. 2, the 35S:Cg1 poplar lines exhibited phenotypes including enlarged, darkened stipules and an increase in the number of branches (sylleptic shoots) and leaves. The number of nodes remained unchanged in many of the transgenic lines.

FIG. 3 shows a summary of the phenotypes of two of the 35S:Cg1 lines (Cg-28 and Cg-29), as compared to a wild-type line and the Cg-10 transgenic line. FIG. 5 illustrates the severity of phenotype effects related to Cg1 expression level, which is indicative of the position effects of T-DNA insertion. The wild-type line examined is WT 717. The 35S:Cg1 lines examined are Cg-10, Cg-29, and Cg-28. (With regard to the nomenclature of the samples, the FIG. 3 and FIG. 5 lines with a "Cg-" suffix number corresponding to a "Cg1-" suffix number in FIG. 1 represent the same line. For example, "Cg1-10" in FIG. 1 is the same line as "Cg-10" in FIG. 3 and FIG. 5.)

FIG. 4 shows the internode length of the wild-type line and the three transgenic 35S:Cg1 lines.

FIG. 5 shows branching and Cg1 expression of the wild-type line and the three transgenic 35S:Cg1 lines discussed above. Additionally, FIG. 5 also shows data for transgenic lines Cg-8, Cg-11, Cg-21, Cg-42, Cg-43, Cg-31, Cg-165, Cg-180, and Cg-181.

FIG. 6 shows lignin analyses from the wild-type control and from 35S:Cg1 transgenic lines Cg-10 (calibrator), Cg-31, Cg-28, and Cg-29. The 35S:Cg1 transgenic plants show reduced levels of total lignin.

In the examples shown herein, the relative amount of syringyl (S) as compared to guaiacyl (G) (the S/G ratio) does not seem to be significantly changed from the wild-type control or is decreased in comparison to the wild-type control. However, in other embodiments of the present invention, miRNA transgenic plants are produced having increased S in the lignin relative to the amount of G. In some embodiments, the total amount of lignin is decreased and the lignin contains an increased S/G ratio as compared to wild-type plants. In some embodiments, the total amount of lignin is decreased and the lignin contains a decreased S/G ratio as compared to wild-type plants.

It is thought that one target of Cg1 could be genes containing the highly conserved SBP box. "SBP" refers to the SQUAMOSA PROMOTER BINDING PROTEIN (SBP)-box family of transcription factors and is a highly conserved DNA binding domain. Currently, it is known that there are at least 14 genes in poplar that contain SBP boxes.

FIG. 7 shows an analysis of SBP gene expression levels in various tissues of wild-type poplar. The SBP genes examined include SBP4 and SBP5, with levels of TUA2 detected as a loading control. There is some expression of SBP4 in all tissues examined except for shoot apex, while there is little to no expression of SBP5 in all of the tissues.

Poplars expressing Cg1 may have commercial value as a cellulosic feedstock for biofuel production, and in the paper-making industry. As noted above, Cg1, which is a member of the miR156 family, contains tandem miR156 genes. Over-expression of Cg1 in poplar leads to reduced lignin levels. The tandem miR156 genes appear to target genes containing the highly conserved SBP box. It has yet to be determined whether miR156 directly regulates lignin biosynthesis. It is possible that the observed reduction in lignin content was an indirect consequence of the developmental changes caused by Cg1 over-expression.

Although this description mainly refers to using embodiments of the invention in conjunction with the Cg1 gene, it should be appreciated that these embodiments may be used to insert other miRNAs into poplar for modulating or altering lignin content or composition.

miRNA over-expression offers a novel approach to altering lignin content or composition in poplar. Other traits regulated by miRNAs are commercially useful too. Multiple stems are desirable due to ease of harvesting and the equipment needs of growers. Rapid growth provides increased biomass yield. Better rooting provides improved establishment rates. Higher sugar levels and control of flowering are also commercially attractive traits. Further embodiments of the invention can be used to insert other miRNAs into poplar for achieving traits other than alteration of lignin content or composition.

Specific embodiments of the invention are described herein. Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments and combinations of embodiments are intended to be included within the scope of the appended claims. Although specific terms are employed herein, they are used in a generic and descriptive sense only and not for purposes of limitation.

What is claimed is:

1. A method of producing a poplar plant with decreased lignin content as compared to a control poplar plant, comprising:
   inserting a *Zea mays* Cg1 gene into a Cg1 construct, wherein the Cg1 gene targets a gene having an SBP box;
   introducing the Cg1 construct into a cell to yield a transformed cell;
   generating a transgenic poplar plant from the transformed cell; and
   growing the transgenic poplar plant, wherein the transgenic poplar plant exhibits decreased lignin content as compared to the control poplar plant.

2. A method of producing a poplar plant with decreased lignin content as compared to a control poplar plant, comprising:
   inserting a *Zea mays* Cg1 gene into a Cg1 construct;
   introducing the Cg1 construct into a cell to yield a transformed cell;
   generating a transgenic poplar plant from the transformed cell; and
   growing the transgenic poplar plant, wherein the transgenic poplar plant exhibits decreased lignin content as compared to the control poplar plant, wherein the insertion of the Cg1 gene results in transgenic popular plants having multiple stems that do not produce flowers.

3. A transgenic poplar plant comprising a *Zea mays* Cg1 gene.

4. The transgenic poplar plant of claim 3 further comprising having multiple stems that do not produce flowers.

5. The transgenic poplar plant of claim 3 further comprising having reduced lignin content as compared to a control poplar plant that does not comprise the *Zea mays* Cg1 gene.

6. A transgenic poplar plant comprising a polynucleotide comprising: (a) SEQ ID NO: 1, (b) the full-length complement of SEQ ID NO: 1, or (c) the reverse full-length complement of SEQ ID NO: 1.

7. A transgenic poplar plant comprising of (a) SEQ ID NO: 1, (b) the full-length complement of SEQ ID NO: 1, or (c) the reverse full-length complement of SEQ ID NO: 1, and having reduced lignin content.

8. A method of producing a transgenic poplar plant according to claim 3, comprising:

inserting the *Zea mays* Cg1 gene into a construct;

introducing the construct into a cell to yield a transformed cell;

generating a transgenic poplar plant from the transformed cell; and growing the transgenic poplar plant, wherein the transgenic poplar plant exhibits decreased lignin content as compared to a control poplar plant.

9. The method of claim 8, wherein the construct comprises a promoter configured to over-express the gene encoding the miRNA in the transgenic poplar plant compared to the control poplar plant.

10. The method of claim 8, wherein the transgenic poplar plant exhibits multiple stems that do not produce flowers as compared to the control poplar plant.

11. The method of claim 8, wherein the miRNA targets a gene containing an SBP box.

12. A method of producing a poplar plant with decreased lignin content as compared to a control poplar plant, comprising:

inserting a *Zea mays* Cg1 gene into a Cg1 construct, wherein the Cg1 construct comprises a constitutive promoter configured to over-express the Cg1 gene in the transgenic poplar plant compared to the control poplar plant:

introducing the Cg1 construct into a cell to yield a transformed cell;

generating a transgenic poplar plant from the transformed cell; and growing the transgenic poplar plant, wherein the transgenic poplar plant exhibits decreased lignin content as compared to the control poplar plant.

13. The method of claim 12, wherein the Cg1 gene comprises (a) SEQ ID NO: 1, (b) the full-length complement of SEQ ID NO: 1, or (c) the reverse full-length complement of SEQ ID NO: 1.

* * * * *

SEQUENCE LISTING

<160> NUMBER OF SEQ ID NOS: 3

<210> SEQ ID NO 1
<211> LENGTH: 764
<212> TYPE: DNA
<213> ORGANISM: Zea mays

```
<400> SEQUENCE: 1
accacccaaa taagcataaa tagtagtggt tgattgtgta attccagaga tataaacgaa      60
tatctctaga grtctgcctc gtcaatagct gcagtatttg ctagccacat atatatacac    120
agttccacac gtagttataa cagaagagag aaggaaagag agaggcagag ttactgcaaa    180
ccatcagtag ttctatgatt ttayttttgc cgttttgttg ctgtttatca tggtgtttga    240
ttgtagggtg gaggagaggt gaaagctgac agaagagagt gagcacacat ggtgcctttc    300
ttgcatgatg tatgatcgag agagttcatg ctcgaagcta tgcgtgctca cttctctctc    360
tgtcagccat tagaactcct ctatctctca atctcgatct ccctctttct tcgttgatct    420
ctcccatggt gatatttatt tgcttcctac acgtgttgtg ttctctttct tgagcacaca    480
cacaacctgt tcatgttgcc ttagggttaa gtttttgcac tttgcgtgaa catggaaaga    540
caaacagtrg atgggttttt ttgaaggttt gacagaagag agtgagcaca cacggtggtt    600
tcttaccatg agtgccatgc taggagctgt gcgtgctcac cctctatctg tcagtcactt    660
catcaagccc atctgtctta gcttgtttcc ggctttccgc tgctaataaa tattctagac    720
tcaagtttat ttgacacaga gatcgatcgc tatcatgttc gatg                     764

<210> SEQ ID NO 2
<211> LENGTH: 27
<212> TYPE: DNA
<213> ORGANISM: Artificial Sequence
<220> FEATURE:
<223> OTHER INFORMATION: primer

<400> SEQUENCE: 2
ccggaaacaa gctaagacag atgggct                                         27

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3
ctgcctcgtc aatagctgca gtatttgc                                        28
```